United States Patent
Lewis et al.

(10) Patent No.: US 8,715,285 B2
(45) Date of Patent: May 6, 2014

(54) PECTUS BAR STABILIZER

(71) Applicant: Biomet Microfixation, LLC, Jacksonville, FL (US)

(72) Inventors: Derek S. Lewis, Jacksonville, FL (US); Shawn D. Roman, Orange Park, FL (US)

(73) Assignee: Biomet Microfixation, LLC, Warsaw, IN (US)

( * ) Notice: Subject to any disclaimer, the term of this patent is extended or adjusted under 35 U.S.C. 154(b) by 0 days.

(21) Appl. No.: 13/662,975

(22) Filed: Oct. 29, 2012

(65) Prior Publication Data

US 2013/0204310 A1    Aug. 8, 2013

Related U.S. Application Data

(63) Continuation of application No. 11/402,319, filed on Apr. 11, 2006, now abandoned.

(60) Provisional application No. 60/680,851, filed on May 13, 2005.

(51) Int. Cl.
    *A61B 17/88*    (2006.01)

(52) U.S. Cl.
    USPC ............................ 606/71; 606/86 R; 606/905

(58) Field of Classification Search
    USPC ............ 606/60, 70–71, 86 R, 237, 280–281, 606/324, 905
    See application file for complete search history.

(56) References Cited

U.S. PATENT DOCUMENTS

| | | |
|---|---|---|
| 212,242 A | 2/1879 | Loper |
| 2,616,328 A | 11/1952 | Kingsmore |
| 3,946,728 A | 3/1976 | Bettex |
| 4,082,332 A | 4/1978 | Palmer |
| 4,201,215 A | 5/1980 | Crossett et al. |
| 4,202,327 A | 5/1980 | Glancy |
| 4,327,715 A | 5/1982 | Corvisier |
| 5,605,364 A | 2/1997 | Shelledy |
| 5,755,808 A | 5/1998 | DeCarlo et al. |
| 6,005,018 A | 12/1999 | Cicierega et al. |
| 6,007,538 A | 12/1999 | Levin |
| 6,024,759 A | 2/2000 | Nuss et al. |
| 6,306,136 B1 | 10/2001 | Baccelli |
| 6,355,038 B1 | 3/2002 | Pisharodi |
| 6,656,179 B1 | 12/2003 | Schaefer et al. |
| 6,689,134 B2 | 2/2004 | Ralph et al. |
| 6,872,210 B2 | 3/2005 | Hearn |
| 2002/0143336 A1 | 10/2002 | Hearn |
| 2004/0116931 A1 | 6/2004 | Carlson |
| 2004/0117016 A1 | 6/2004 | Abramson |
| 2004/0204713 A1 | 10/2004 | Abdou |
| 2006/0058786 A1 | 3/2006 | Kim et al. |
| 2006/0089648 A1 | 4/2006 | Masini |

FOREIGN PATENT DOCUMENTS

| | | |
|---|---|---|
| EP | 0583520 A1 | 2/1994 |
| WO | WO-2004028412 A1 | 4/2004 |

OTHER PUBLICATIONS

European Search Report for European Patent Application No. 06009368, dated Sep. 15, 2006.

*Primary Examiner* — Nicholas Woodall
*Assistant Examiner* — Larry E Waggle, Jr.
(74) *Attorney, Agent, or Firm* — Harness, Dickey

(57) ABSTRACT

A pectus bar stabilizer assembly and method includes a first base part separable from a second base part. The first and second base parts combine to define a channel therebetween. A pectus bar is received by the channel and a retainer assembly retains the pectus bar in the channel.

20 Claims, 15 Drawing Sheets

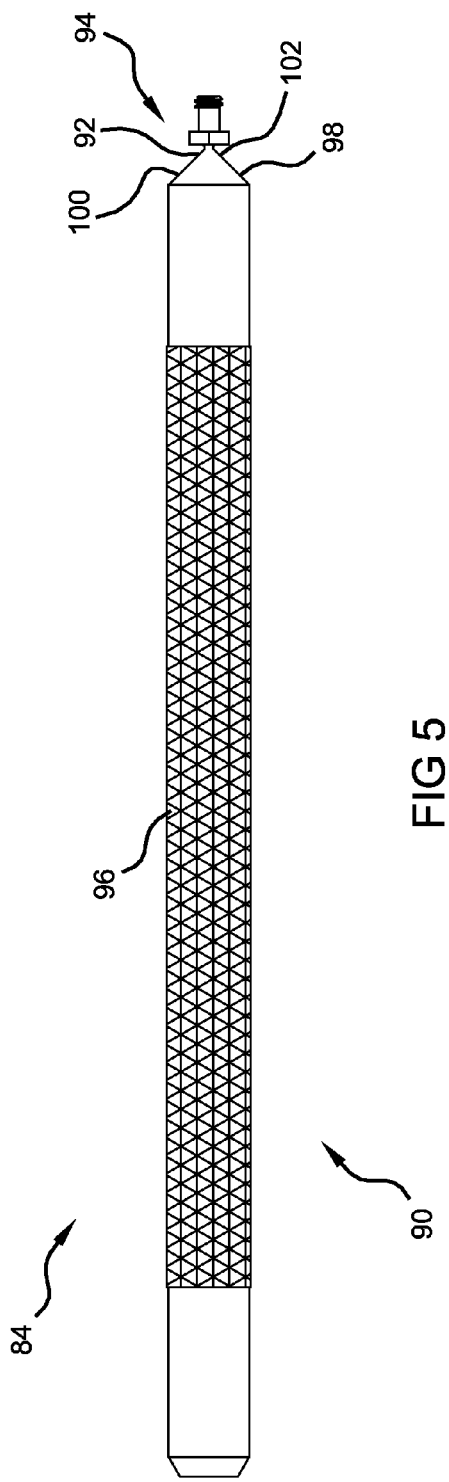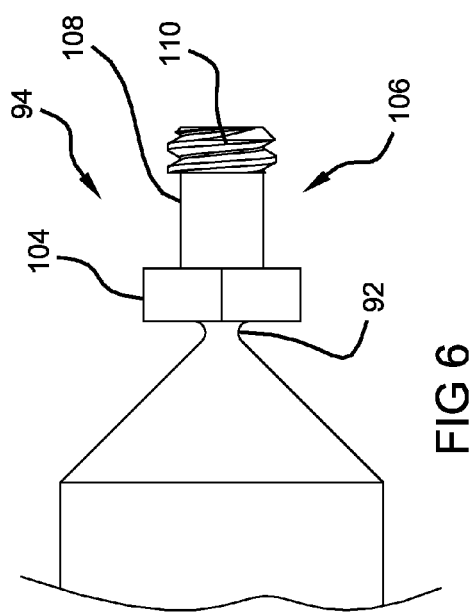

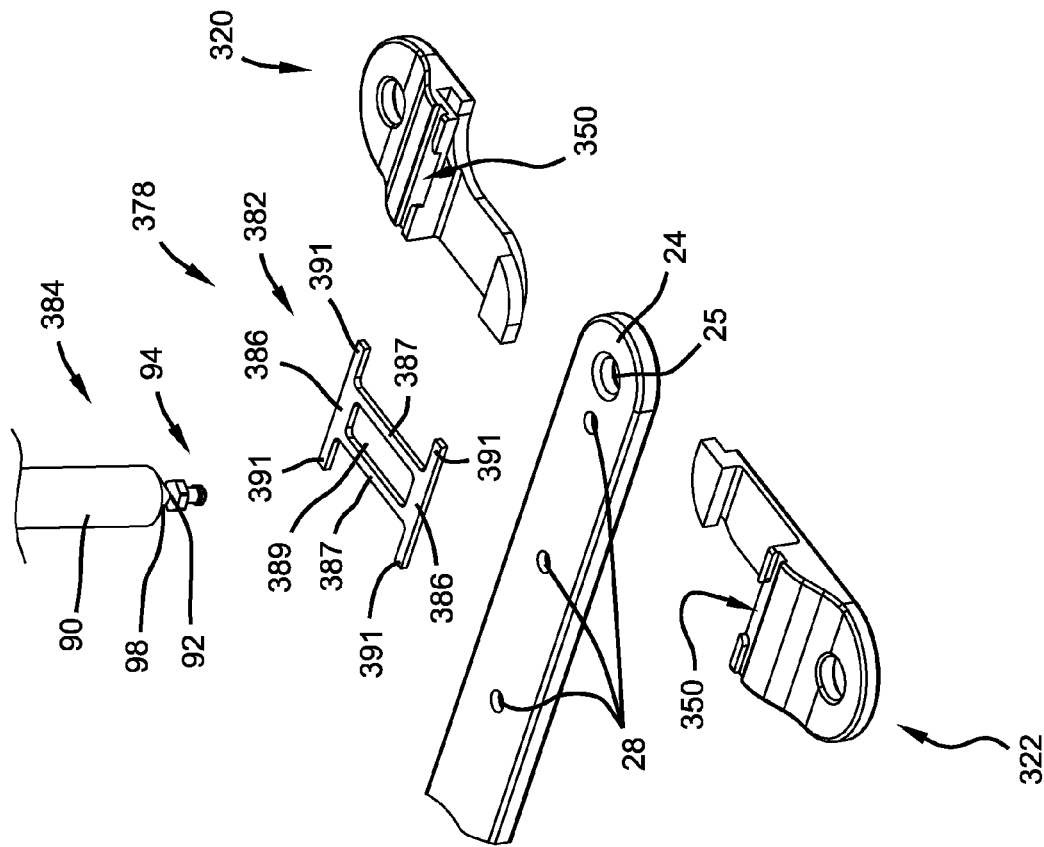
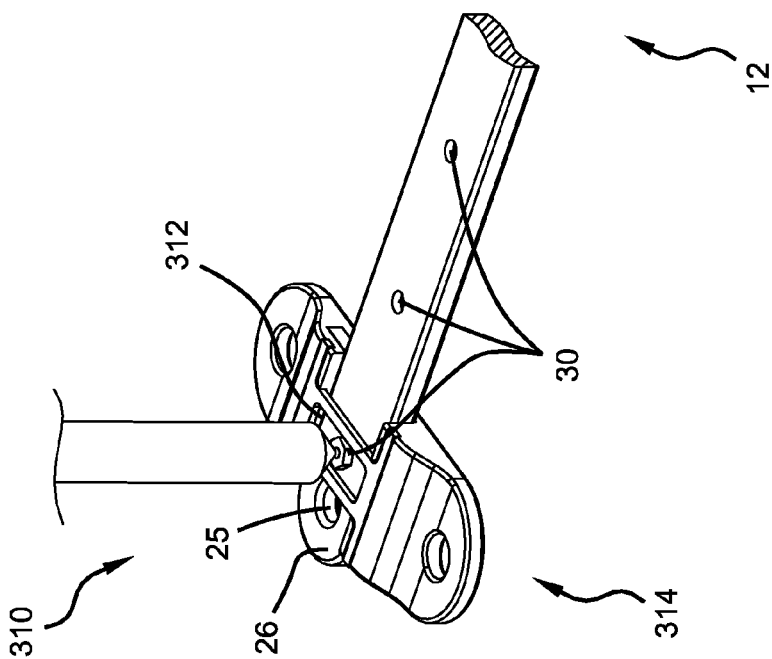
FIG 13

PECTUS BAR STABILIZER

CROSS-REFERENCE TO RELATED APPLICATIONS

This application is a continuation of U.S. patent application Ser. No. 11/402,319 filed on Apr. 11, 2006, which claims the benefit of U.S. Provisional Application No. 60/680,851, filed on May 13, 2005. The entire disclosures of each of the above applications are incorporated herein by reference.

FIELD

The present teachings relate to an apparatus for the correction of chest wall deformities, and more specifically to a pectus bar stabilizer.

BACKGROUND

To correct chest wall deformities, a pectus bar may be fixedly mounted to supporting structure, typically cartilage, using a stabilizer plate, which generally includes a single plate having a recess through a central portion and apertures therein for receiving and fixedly attaching a pectus bar thereto. A pectus bar stabilizer may also include a series of apertures on distal portions for fixedly securing the stabilizer plate to the supporting structure. To remove or adjust the pectus bar, screws securing the pectus bar to the stabilizer plate must be removed. But the screws are often difficult to access and remove due to surrounding tissue or bone growth.

SUMMARY

A pectus bar stabilizer assembly generally includes a pectus bar, a retainer assembly, a first base part and a second base part. The first and second base parts are separable from one another to facilitate removal and combinable to define a channel therebetween. The pectus bar is received by the channel and the retainer assembly retains the pectus bar in the channel. A portion of the retainer assembly may be removed, allowing the pectus bar to be removed or adjusted.

Further areas of applicability of the present teachings will become apparent from the detailed description provided hereinafter. It should be understood that the detailed description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 5 is a plan view of the tool and stopping member;

FIG. 6 is a partial plan view of the tool and stopping member;

FIG. 13 is a perspective view of a pectus bar stabilizer assembly shown partially assembled and partially exploded;

DETAILED DESCRIPTION

Figure 1:
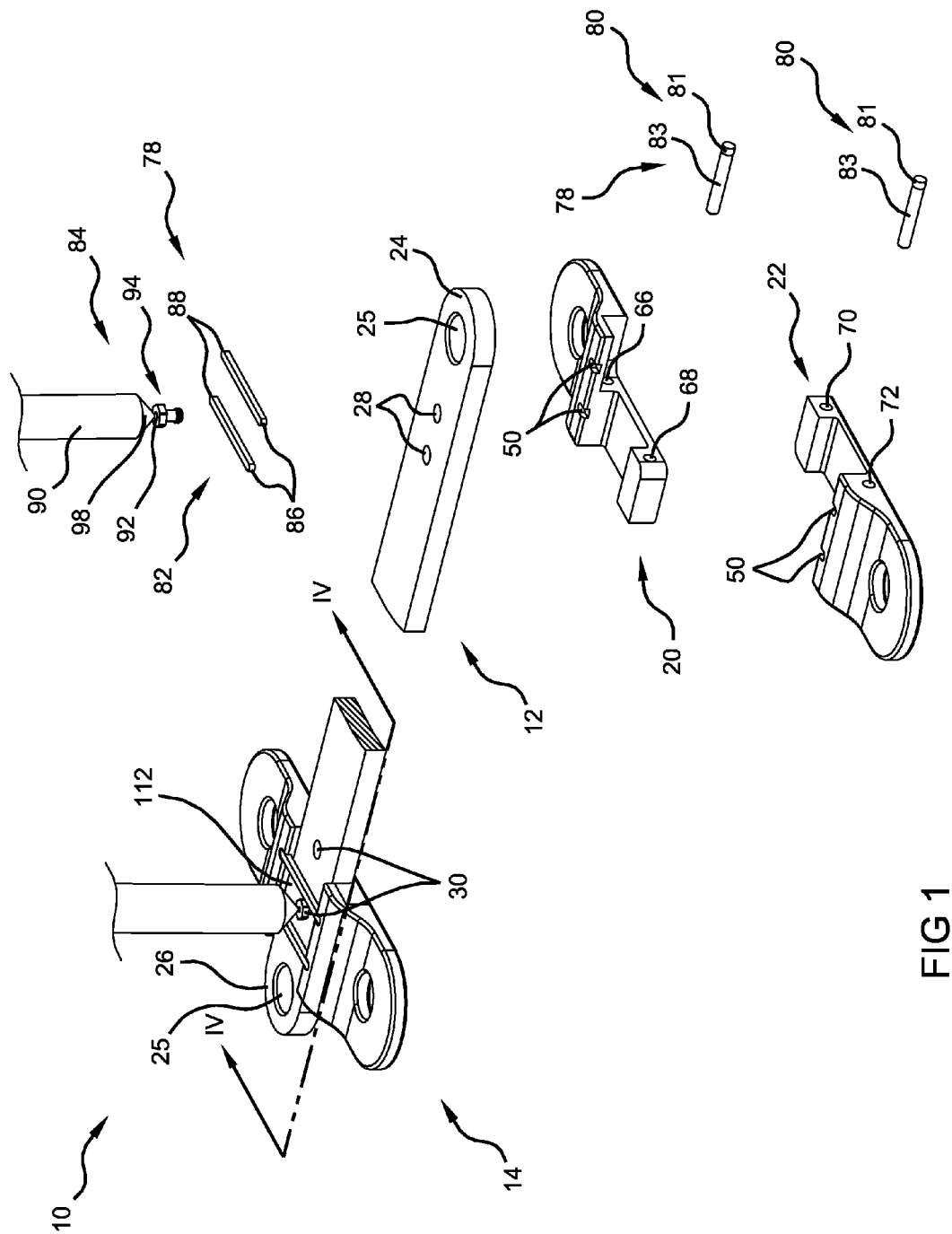
FIG. 1 is a perspective view of a first pectus bar stabilizer assembly shown partially assembled and partially exploded.

FIGS. 1-4 show a pectus bar stabilizer assembly 10 generally includes a pectus bar 12 and a pectus bar stabilizer 14. The pectus bar stabilizer 14 retains the pectus bar 12 and may be fixedly attached to an external structure, such as cartilage.

The pectus bar 12 may have a longitudinally extending bar of generally uniform thickness, a generally rectangular cross-section, and an end portion 24 opposite a second end portion 26. The first and second end portions 24, 26 may include an arcuate periphery and an aperture 25. A series of apertures 28, 30, which may include internal threads, may be disposed inwardly from the end portions 24, 26.

The pectus bar stabilizer 14 may include first and second base parts 20, 22 and a retainer assembly 78. The first and second base parts 20, 22 may be generally similar to one another, with minor differences that will be discussed below. For simplicity in the description, first base part 20 will be discussed in detail.

The first base part 20 may include a body portion 32 and a leg 34 extending therefrom. The body portion 32 may include an inner body wall 36, a top body surface 38, a lower body surface 40 and an outer body surface 42. The top body surface 38 may include three main sections 44, 46, 48. The first section 44 is generally planar and includes a series of notches 50. The second section 46 is contoured and slopes downward from the first section 44 to the third section 48. The third section 48 is generally planar and extends from the second section 46. The lower body surface 40 is generally planar and generally parallel to the first and third sections 44, 48 of the top body surface 38. The outer body surface 42 connects the top body surface 38, the lower body surface 40 and the inner body wall 36.

The inner body wall 36 may include two sections 56, 58. The first section 56 is generally rectangular and has a width L1 and a height L2. The second section 58 is generally rectangular and has a width L1 and a height L3. The height L3 of the second section 58 is less than the height L2 of the first section 56. A recess 60, defined below the second section 58 and proximate the first section 56, extends into the body portion 32 a depth of L4 and has a width L1 and a height L5.

Figure 7:
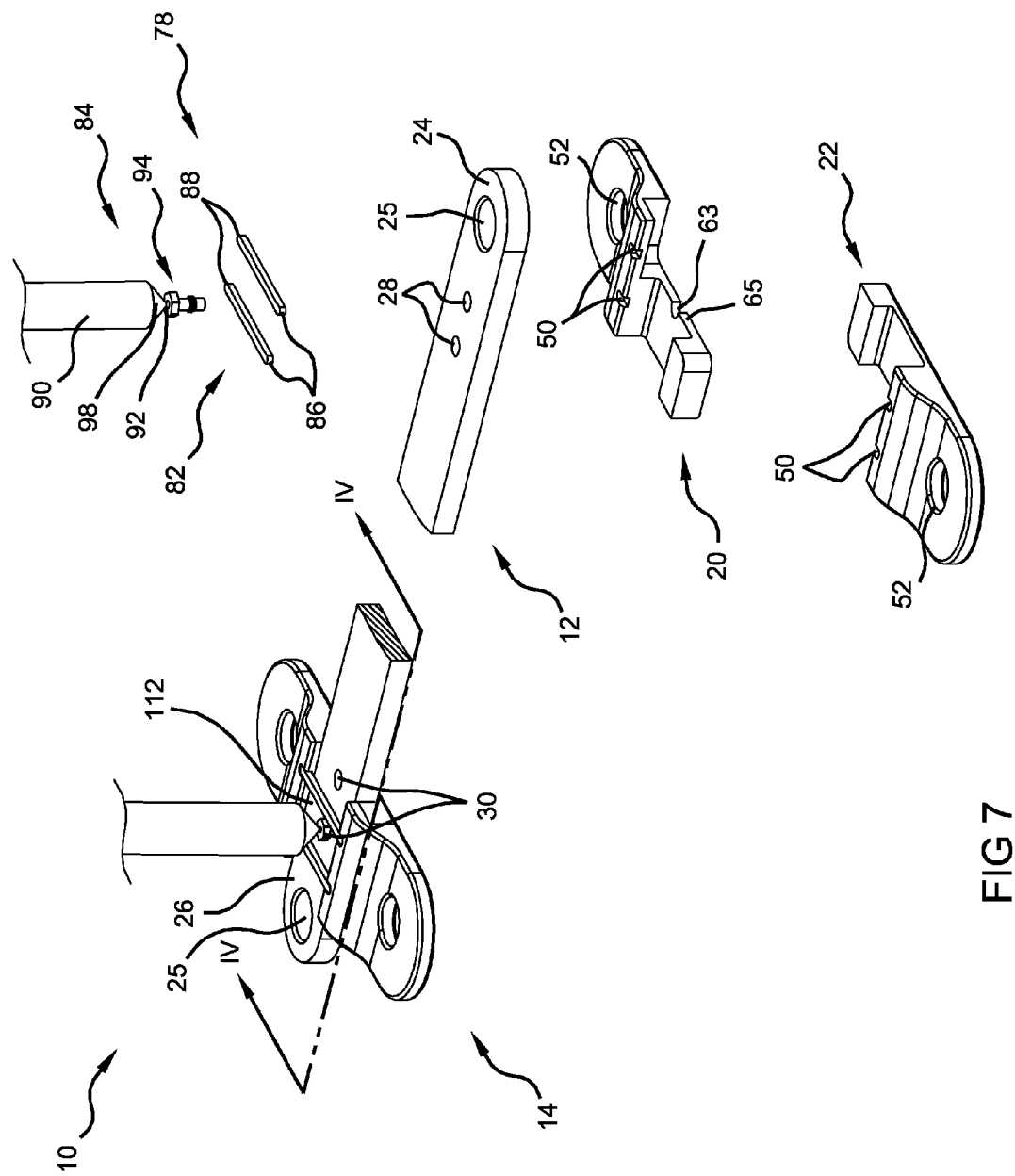
FIG. 7 is a perspective view of a pectus bar stabilizer assembly shown partially assembled and partially exploded.
Figure 8:
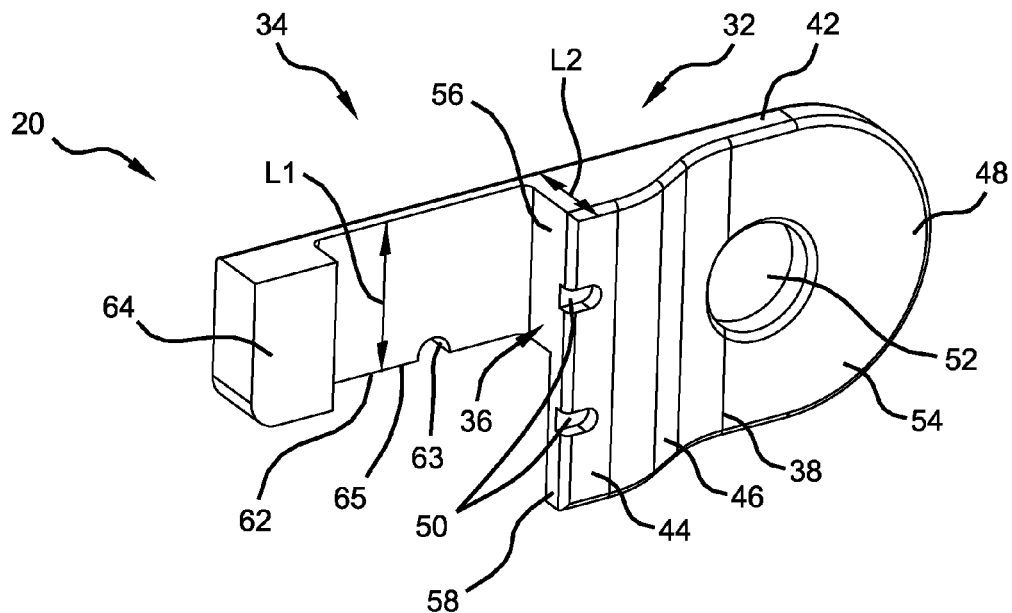
FIG. 8 is a front perspective view of one base part of the pectus bar stabilizer shown in FIG. 7.
Figure 9:
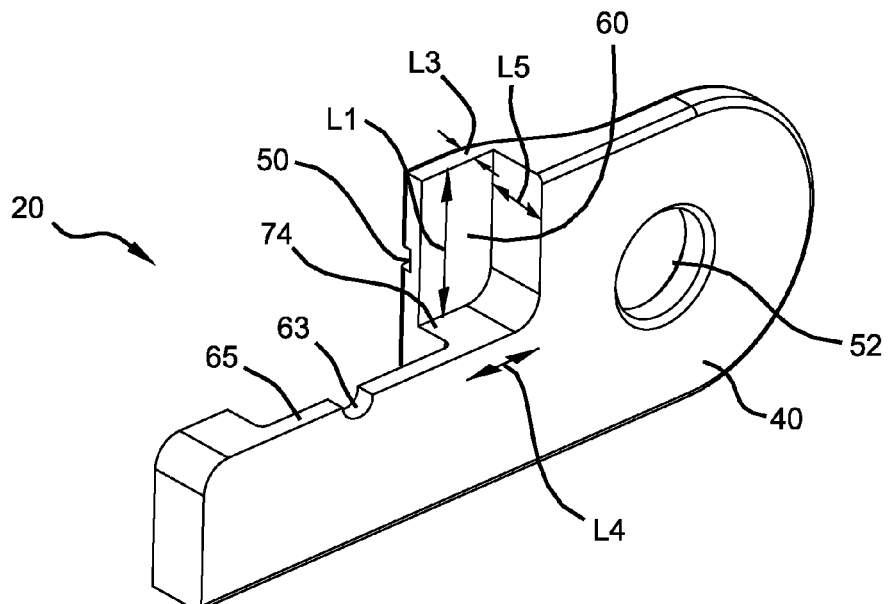
FIG. 9 is a rear perspective view of the base part of FIG. 8.

A leg 34 extends generally perpendicularly from the first section 56 of the inner body wall 36. The leg 34 may have a width generally equal to the width L1 of the first section 56 of the inner body wall 36 and may be divided into a first leg portion 62 and a second leg portion 64. The first leg portion 62, which is located proximate the body portion 32, may have a generally rectangular cross-section and a height less than the height L5 of the recess 60 in the body portion 32. The first leg portion 62 of the first and second base parts 20, 22 may also each include an arcuate recess 63 at an inner edge portion 65 as shown in FIGS. 7-9. The second leg portion 64 may have a generally rectangular cross-section and may be sized to generally fit within the recess 60, having a height, length and width generally corresponding to the dimensions L5, L4, L1 of recess 60.

Figure 4:
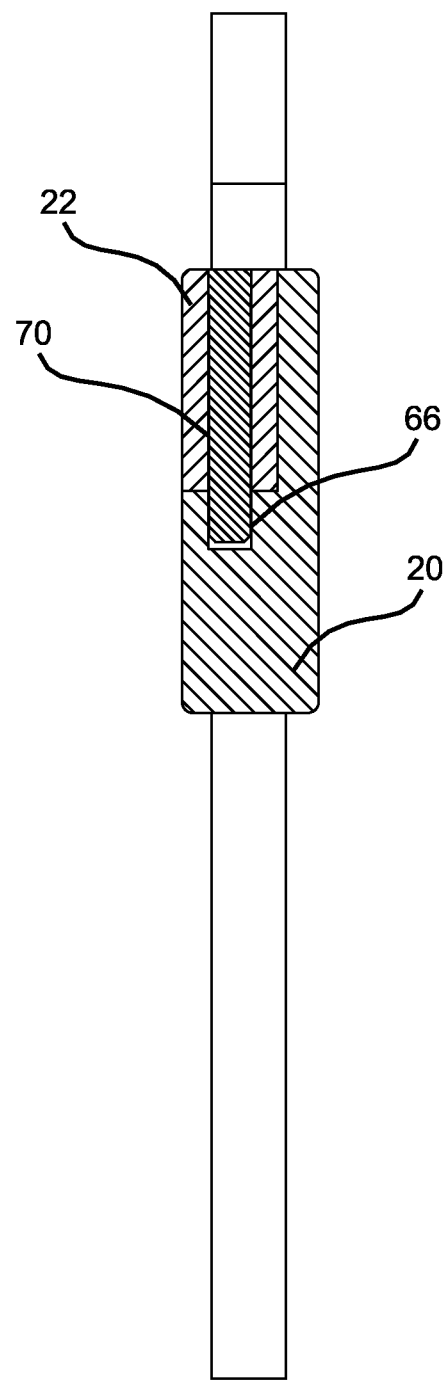
FIG. 4 is a sectional view of the base parts of the pectus bar stabilizer as cut along line IV-IV of FIG. 1.

A series of apertures may be located in the first base part 20. A first aperture 52 may be located at a distal end 54 of the body portion 32, passing through the third section 48 of the top body surface 38 and the lower body surface 40. The first aperture 52 allows the first base part 20 to be coupled to a supporting structure, such as cartilage. A series of pin apertures 66, 68, 70, 72 may be provided in the first and second base parts 20, 22. The pin apertures 66, 68 extend partially into the first base part 20. The first pin aperture 66 extends into body portion 32 through the recess side wall 74 in the recess 60 of body portion 32. The second pin aperture 68 extends into the second leg portion 64 through the second leg portion side wall 76. The pin apertures 70, 72 in the second base part 22 may be positioned similarly to those in the first base part 20, and may extend completely through the second leg portion 64 and the body portion 32 of the second base part 22, as shown in FIG. 4. Alternatively, the base parts 20, 22 may not include any pin apertures, eliminating the need for pins as shown in FIGS. 7-9.

The retainer assembly 78 may include a series of pins 80, a series of retaining bars 82 and a stopping member assembly 84. The pins 80 may be generally cylindrical members, sized to be located within the pin apertures 66, 68, 70, 72. The pin may include a first portion 81 and a main portion 83 generally extending therefrom. The first portion 81 of the pin 80 may have a diameter greater than the diameter of the main portion 83 of the pin 80. The main portion 83 of the pin 80 may be smaller in diameter than the pin apertures 66, 68, 70, 72. The main portion 83 may be first inserted into the pin apertures 66, 68, 70, 72. The first portion 81 may have a diameter similar to the diameter of the pin apertures, resulting in retention of the pin within the pin apertures 66, 68, 70, 72, due to friction between the first portion 81 and pin apertures 70, 72.

The retaining bars 82 may include a first end portion 86 opposite a second end portion 88. The retaining bars 82 may generally have flattened, substantially rectangular cross-sections with rounded edges at the first and second end portions 86, 88. The retaining bars 82 may have a generally uniform thickness throughout their length. The first and second ends 86, 88 of the retaining bars 82 may be located in the notches 50 in the body portions 32 of the base parts 20, 22.

The stopping member assembly 84, shown in FIGS. 5 and 6, may include a tool 90, a neck portion 92 and a stopping member 94. The tool 90 is generally cylindrical and may include a knurled surface 96 to facilitate grasp by a user. A distal end 98 of the tool 90 may be generally conical, having a greater diameter at a first end 100 and a reduced diameter at a second end 102. A neck portion 92 may generally extend from the distal end 98 of the tool 90 to the stopping member 94. The neck portion 92 may be substantially smaller in diameter than both the tool 90 and the stopping member 94 and provides a mechanism to separate the tool 90 from the stopping member 94. The separation feature may be a necked-down portion facilitating separation by bending or twisting the tool 90 relative to the stopping member 94, or may include a torque-limiting feature to sever the tool 90 from the stopping member 94 upon meeting a predetermined torque limit during insertion. The neck portion 92 diameter may be one-tenth of the diameter of the tool 90 and less than one-half of the diameter of the smallest diameter of the stopping member 94. A variation may include a separate tool and stopping member.

The stopping member 94 may include a hexagonal head 104 and a body portion 106 generally extending therefrom. The hexagonal head 104 may be attached to the neck portion 92. The body portion 106 may include an unthreaded portion 108 and a threaded portion 110. The unthreaded portion 108 may be located proximate the hexagonal head 104 and the threaded portion 110 may be located at the end of the body portion 106 distal from the hexagonal head 104.

The pectus bar stabilizer assembly 10 may retain the pectus bar 12 through the first and second base parts 20, 22 and the retainer assembly 78. The two base parts 20, 22 may be placed proximate one another, inserting the second leg portion 64 of the first base part 20 into the recess 60 of the second base part 22 and inserting the second leg portion 64 of the second base part 22 into the recess 60 of the first base part 20. In this configuration, the first and second base parts 20, 22 define a channel 112 bound by the inner body wall 36 of the first base part 20, the inner body wall 36 of the second base part 22 and the first leg portions 62 of the first and second base parts 20, 22. In this configuration, the pin apertures 66, 68, 70, 72 of the first and second base parts 20, 22 are in respective alignment.

Once the first and second base parts 20, 22 have been arranged to define the channel 112, pins 80 may be inserted into the pin apertures 66, 68, 70, 72. The pins 80 may extend completely through the first base part 20 and partially into the second base part 22, securing the first and second base parts 20, 22 to one another in a transverse direction relative to the axis of the pins 80. Next, the retaining bars 82 may be placed over the channel 112. The first and second ends 86, 88 may be located within the notches 50 in the body portion 32 of the first and second base parts 20, 22 and welded in place. The retaining bars 82 secure the first and second base parts 20, 22 to one another in a transverse direction relative to the bars 82.

Once the first and second base parts 20, 22 are fixedly attached to one another, a first end portion 24 of the pectus bar 12 may be inserted into the channel 112 below the retaining bars 82. After the first end portion 24 is located within the channel 112, one of the apertures 28 in the first end portion may be aligned between the retaining bars 82. After the desired aperture 28 is located between the retaining bars 82, the stopping member 94 may be secured in the aperture 28. Once the stopping member 94 is securely in place, the tool 90 is separated from the stopping member 94 at the neck portion 92. The hexagonal head 104 may provide retention of the pectus bar 12. The body portion 106 of the stopping member 94 may be attached to the aperture 28 in the pectus bar 12 and the hexagonal head 104 may extend above the pectus bar 12, preventing the pectus bar 12 from translating axially beyond the retaining bars 82.

Figure 2:
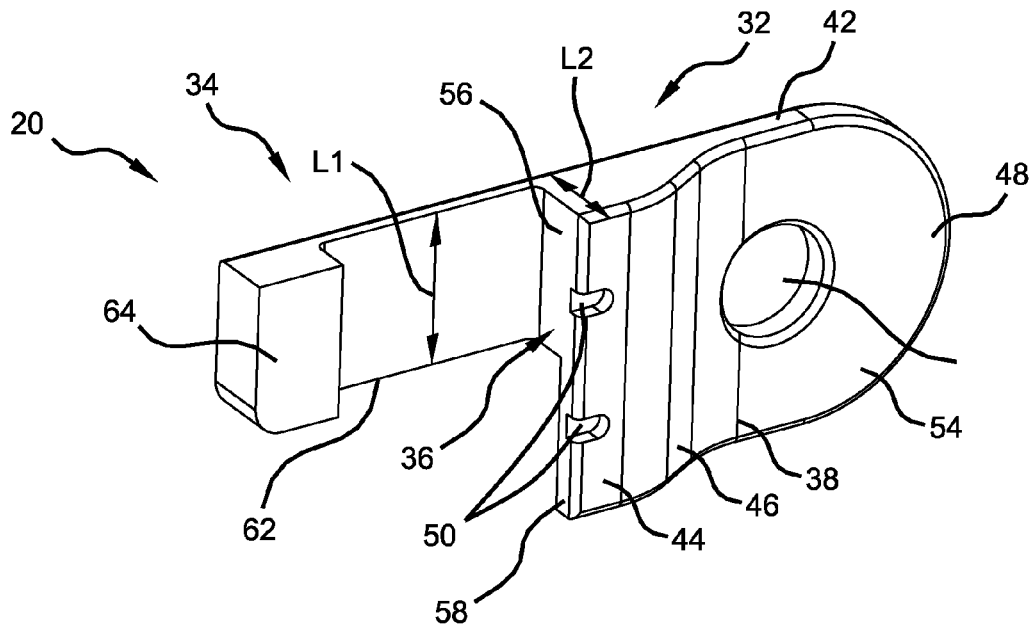
FIG. 2 is a front perspective view of one base part of a pectus bar stabilizer.
Figure 3:
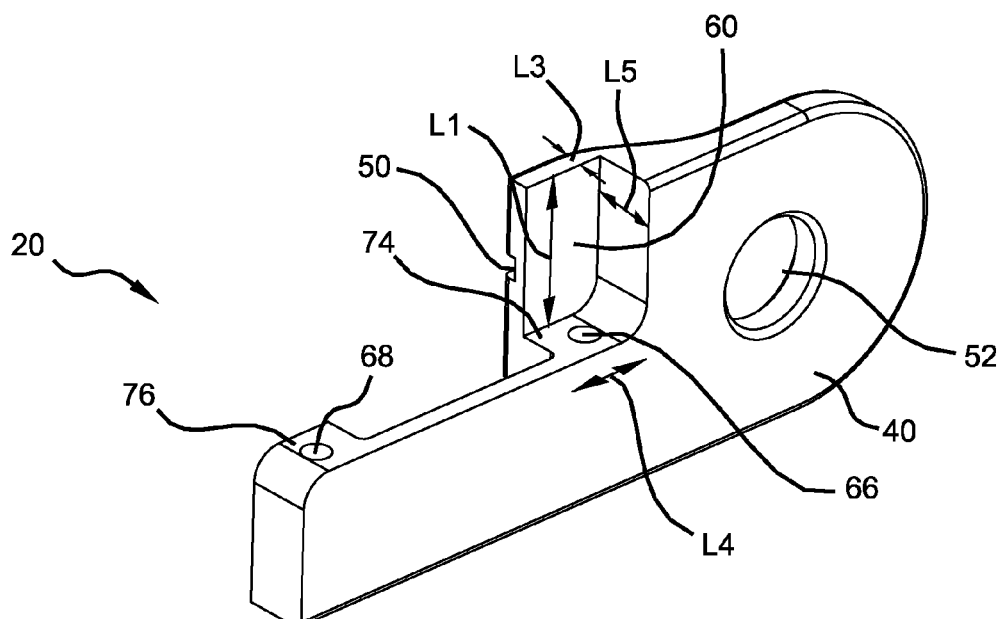
FIG. 3 is a rear perspective view of the base part of FIG. 2.

In FIGS. 1-3, the stopping member 94 is shown only passing through the pectus bar because the channel 112 has no aperture therethrough. As shown in FIGS. 7-9 the channel may have an aperture allowing for passage of the stopping member 94 therethrough, providing further retention. The stopping member 94 may include an additional portion extending beyond the threaded portion 110. This additional portion may be unthreaded, as shown in FIG. 7, or may be threaded.

Other stopping members may be used for retention of the pectus bar 12 within the pectus bar stabilizer 14. One such example is a rivet, which may be applied to an aperture 28 in the pectus bar 12, leaving a head portion exposed above the pectus bar 12 and retaining the pectus bar 12 within the pectus bar stabilizer 14 as described above.

The pectus bar 12 may be removed from the pectus bar stabilizer 14 without removing any of the stopping members 94. One of the retaining bars 82 located distal from the retained end portion 24, 26 may be removed allowing the pectus bar 12 to translate axially in a direction free of the bars 82. Both bars 82 may also be removed to eliminate retention of the pectus bar 82 within the pectus bar stabilizer 14.

The pectus bar stabilizer 14 may generally be attached to an external structure, such as cartilage. The pectus bar stabilizer 14 may be attached using the apertures 52 located in the distal portions of the first and second base parts 20, 22. The attachment may be made using any suitable method including sutures, screws or some other form of attachment.

A typical pectus bar stabilizer assembly 10 may include two pectus bar stabilizers 14, as shown in FIG. 1. The second pectus bar stabilizer 14 may be identical to the first pectus bar stabilizer 14, as described above. A second end portion 26 of the pectus bar 12 may be attached to the second pectus bar stabilizer 14 through a second series of apertures 30 in a manner similar to that described above.

Figure 10:
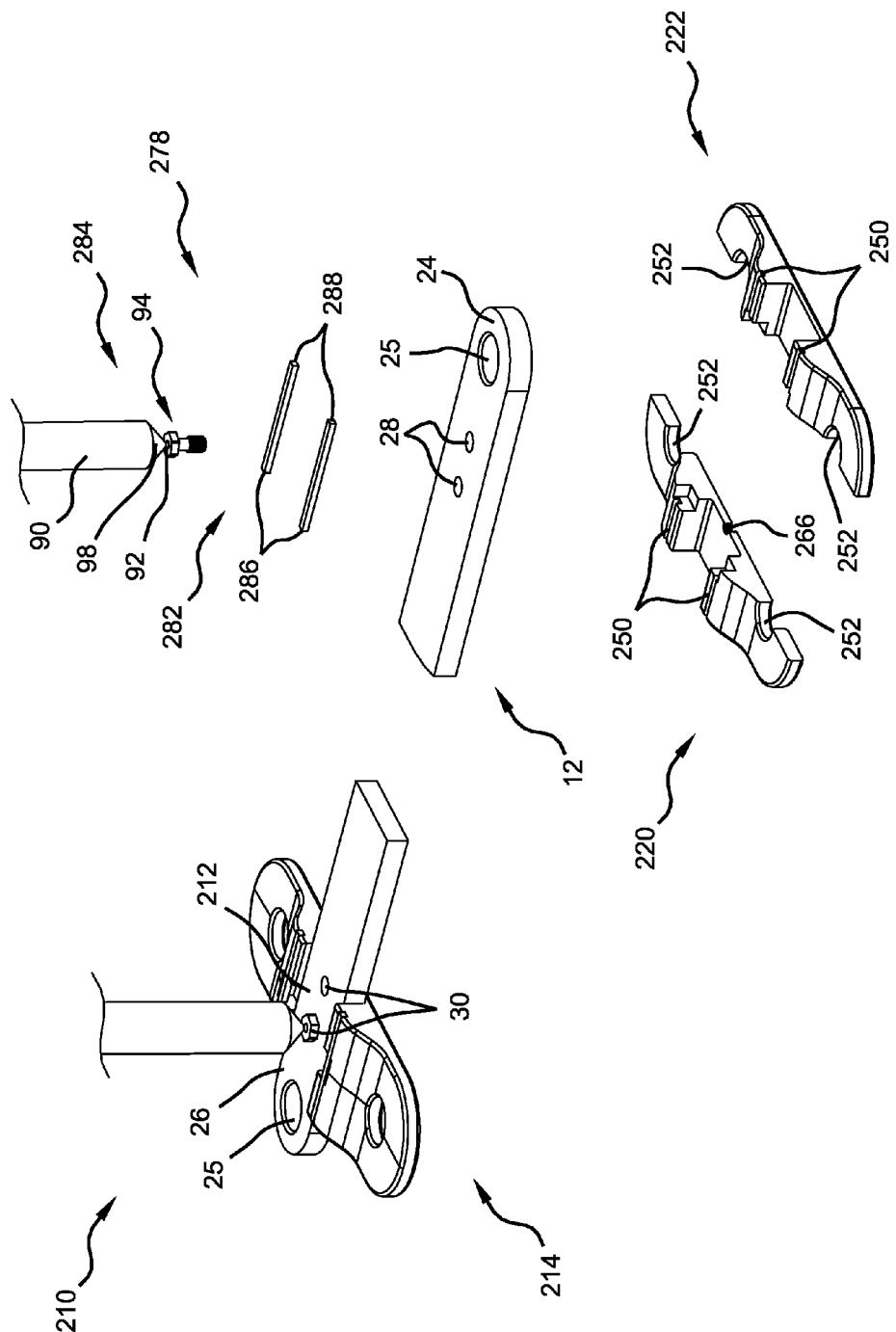
FIG. 10 is a perspective view of a pectus bar stabilizer assembly shown partially assembled and partially exploded.
Figure 11:
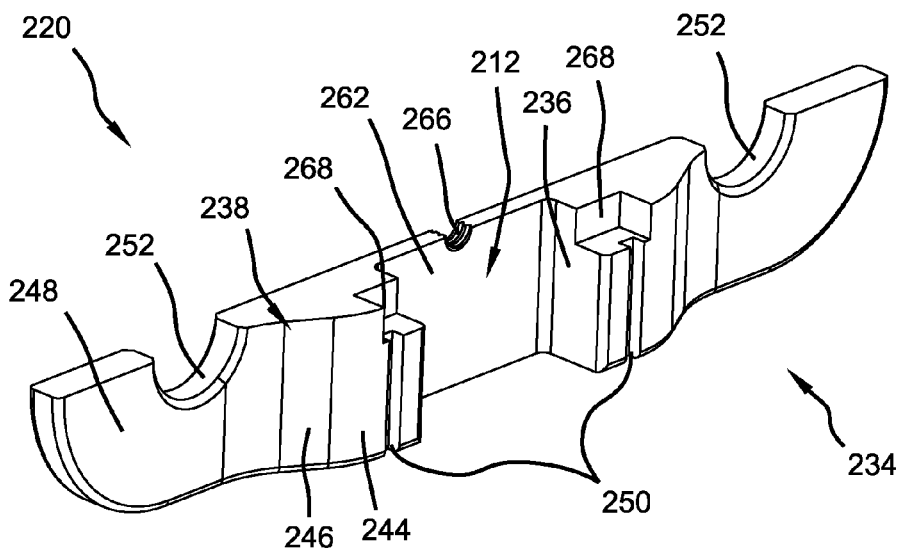
FIG. 11 is a front perspective view of one base part of the pectus bar stabilizer shown in FIG. 10.
Figure 12:
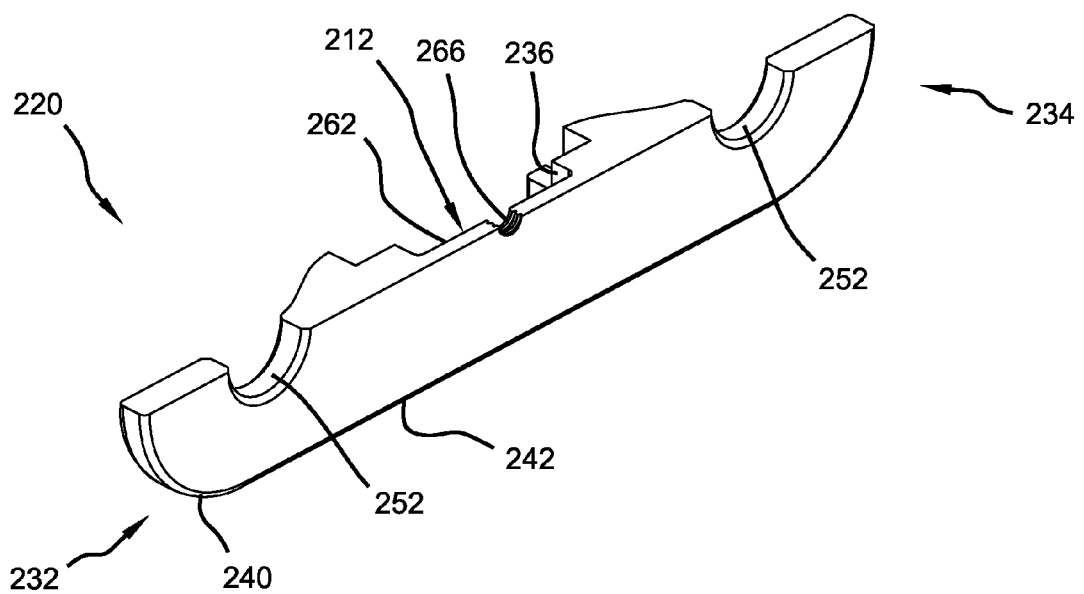
FIG. 12 is a rear perspective view of the base part of FIG. 11.

An additional pectus bar stabilizer assembly 210 is shown in FIGS. 10-12 and generally includes a pectus bar 12 and a pectus bar stabilizer 214. The pectus bar stabilizer 214 retains the pectus bar 12 and may be fixedly attached to an external structure, such as cartilage.

The pectus bar stabilizer 214 may include first and second base parts 220, 222 and a retainer assembly 278. The first and second base parts 220, 222 may be generally similar to one another. For simplicity in the description, only first base part 220 will be discussed in detail with the understanding that the second base part 222 is similar in structure.

The first base part 220 may include a first end 232, a second end 234 and a channel 212 disposed therebetween. The first and second ends 232, 234 are generally similar and only the first end 232 will be discussed in detail. The first end 232 may include an channel wall 236, a top body surface 238, a lower body surface 240 and an outer body surface 242. The top body surface 238 may include three main sections 244, 246, 248. The first section 244 is generally planar and includes a series of notches 250. The second section 246 is contoured and slopes downward from the first section 244 to the third section 248. The third section 248 is generally planar and extends from the second section 246. An arcuate recess 252 is formed through the third section 248 of the top body surface 238. The arcuate recess 252 aligns with a similar arcuate recess 252 on the second base part 222, generally forming an aperture through the first end 232 thereof. The lower body surface 240 is generally planar and generally parallel to the first and third sections 244, 248 of the top body surface 238. The outer body surface 242 connects the top body surface 238, the lower body surface 240 and the channel wall 236.

The channel walls 236 define the width of the channel 212 and the middle portion 262 defines the lower structure of the channel 212. A series of channel notches 268 are located in the channel walls 236 and the first section 244 of the top body surface 238. A threaded arcuate recess 266 may be formed on the inner surface of the middle portion 262. When the first and second base parts 220, 222 are assembled the threaded arcuate recesses 266 of each align, forming a threaded aperture.

The retainer assembly 278 may include a series of retaining bars 282 and a stopping member assembly 284. The retaining bars 282 may include a first end portion 286 opposite a second end portion 288. The retaining bars 282 may generally have flattened, substantially rectangular cross-sections with rounded edges at the first and second end portions 286, 288. The retaining bars 282 may have a generally uniform thickness throughout their length. The first and second ends 286, 288 of the retaining bars 282 may be located in the notches 250 in the first and second ends 232, 234 of the base parts 220, 222.

The stopping member assembly 284 may include a tool 90, a neck portion 92 and a stopping member 94 similar to that described above. The stopping member 94 may include an additional threaded portion extending beyond the threaded portion 110, as shown in FIG. 10.

The pectus bar stabilizer assembly 210 may retain the pectus bar 12 through the first and second base parts 220, 222 and the retainer assembly 278. The two base parts 220, 222 may be placed proximate one another defining a channel 212 bound by the channel walls 236 and middle portion 262. In this configuration, the notches 250 of the first and second base parts 220, 222 are in respective alignment.

Once the first and second base parts 220, 222 have been arranged to define the channel 212, the retaining bars 282 may be placed along the sides if the channel 212. The first and second ends 286, 288 may be located within the notches 250 in the first and second ends 232, 234 of the first and second base parts 220, 222 and welded in place. The retaining bars 282 secure the first and second base parts 220, 222 to one another in both a transverse direction and an axial direction relative to the bars 282.

Once the first and second base parts 220, 222 are fixedly attached to one another, a first end portion 24 of the pectus bar 12 may be inserted into the channel 212. After the first end portion 24 is located within the channel 212, one of the apertures 28 in the first end portion may be aligned with the aperture formed by the threaded arcuate recesses 266 in the middle portion 262. After the desired aperture 28 is located above the aperture formed by the threaded arcuate recesses 266, the stopping member 94 may be threaded into the aperture 28 and through the aperture formed by the threaded arcuate recesses 266 as well. Once the stopping member 94 is securely in place, the tool 90 is separated from the stopping member 94 at the neck portion 92. The hexagonal head 104 may provide retention of the pectus bar 12. The body portion 106 of the stopping member 94 may be attached to both the aperture 28 in the pectus bar 12 and the aperture formed by the threaded arcuate recesses 266. The hexagonal head 104 may extend above the pectus bar 12, providing for removal of the stopping member 94 from the pectus bar 12 if desired.

Other stopping members may be used for retention of the pectus bar 12 within the pectus bar stabilizer 14. One such example is a rivet, which may be applied to an aperture 28 in the pectus bar 12, leaving a head portion exposed above the pectus bar 12 to retain the pectus bar 12 within the pectus bar stabilizer 214 as described above.

The pectus bar 12 may be removed from the pectus bar stabilizer 214 without removing any of the stopping members 94. The retaining bars 282 located distal from the retained end portion 24, 26 may be removed allowing one of the base parts 220, 222 to be removed. The pectus bar 12 may then translate axially in a direction free of the aperture formed by the threaded arcuate recesses 266. The stopping member 94 may also be removed, freeing the pectus bar 12 from the pectus bar stabilizer 214.

The pectus bar stabilizer 214 may generally be attached to an external structure, such as cartilage as previously discussed.

Figure 14A:
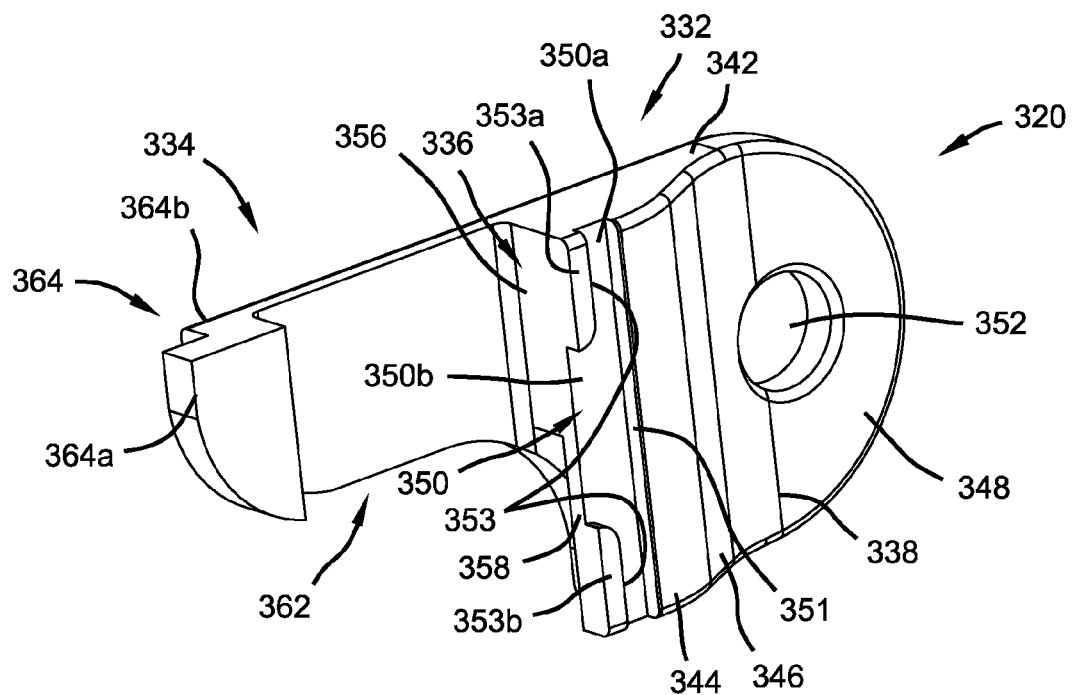
FIG. 14A is a front perspective view of one base part of the pectus bar stabilizer shown in FIG. 13.
Figure 14B:
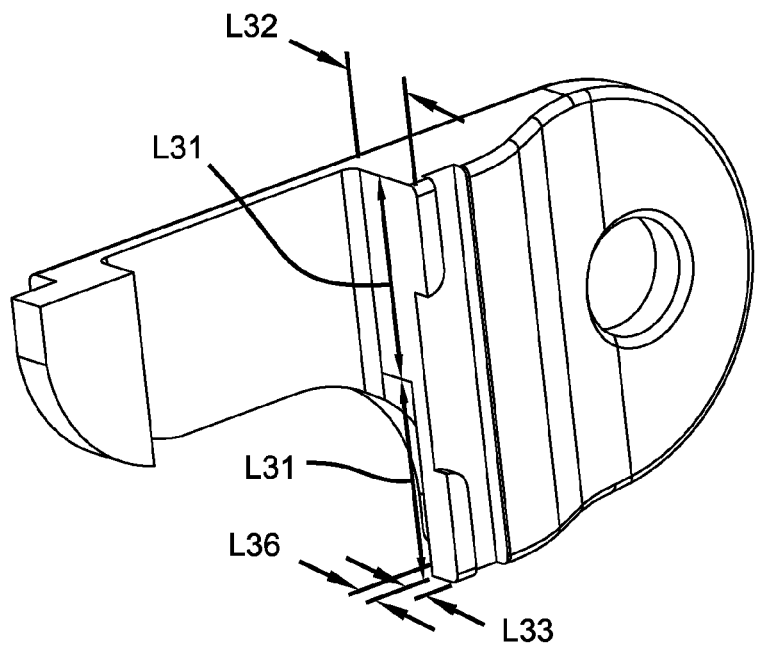
FIG. 14B is an additional front perspective view of the base part of FIG. 14A.
Figure 15A:
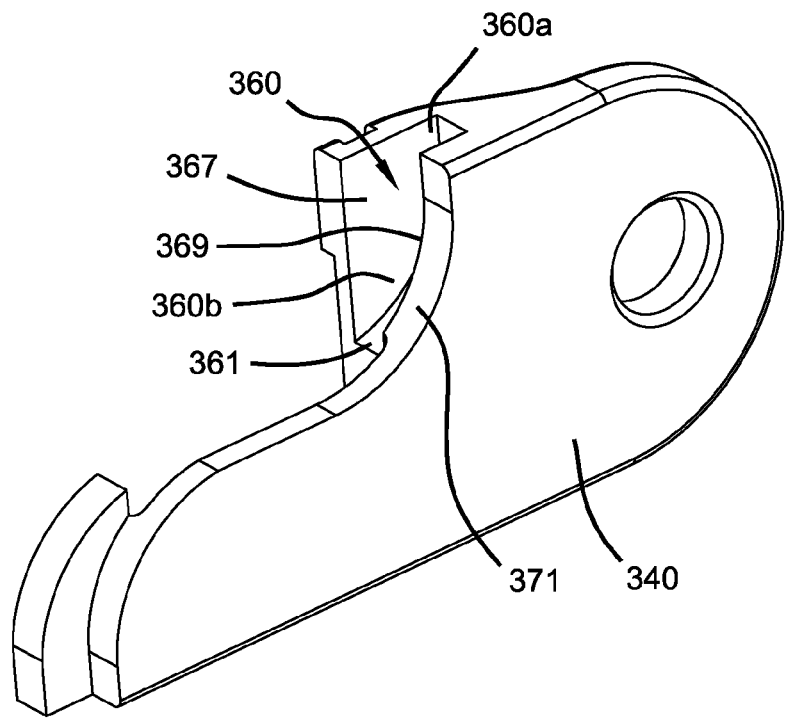
FIG. 15A is a rear perspective view of the base part of FIG. 14.
Figure 15B:
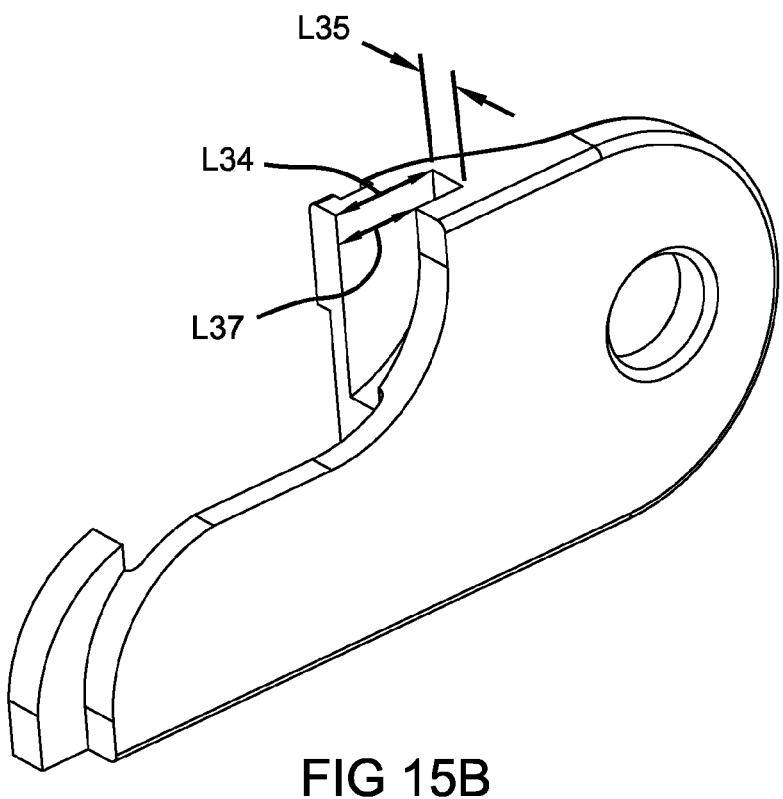
FIG. 15B is an additional front perspective view of the base part of FIG. 15A.

A further example of a pectus bar stabilizer assembly 310 is shown in FIGS. 13-15 and may generally include a pectus bar 12 and a pectus bar stabilizer 314. The pectus bar stabilizer 314 retains the pectus bar 12 and may be fixedly attached to an external structure, such as cartilage.

The pectus bar stabilizer 314 may include first and second base parts 320, 322 and a retainer assembly 378. The first and second base parts 320, 322 may be generally similar to one another. For simplicity in the description, only first base part 320 will be discussed in detail with the understanding that the second base part 322 is similar in structure.

The first base part 320 may include a body portion 332 and a leg 334 extending therefrom. The body portion 332 may include an inner body wall 336, a top body surface 338, a lower body surface 340 and an outer body surface 342. The top body surface 338 may include three main sections 344, 346, 348. The first section 344 is generally planar and includes a retainer recess 350.

The retainer recess 350 may include a first recess 350a forming a channel in the first section 344 that is generally parallel to the inner body wall 336. The first recess 350a may extend the entire width of the first section 344. The first recess 350a may be defined by an outer wall 351 and an inner wall 353 located opposite one another. The inner wall 353 may include two discrete sections 353a, 353b forming an opening 350b therebetween.

The second section 346 is contoured and slopes downward from the first section 344 to the third section 348. The third section 348 is generally planar and extends from the second section 346. The lower body surface 340 is generally planar and generally parallel to the first and third sections 344, 348 of the top body surface 338. The outer body surface 342 connects the top body surface 338, the lower body surface 340 and the inner body wall 336.

The inner body wall 336 may include two sections 356, 358. The first section 356 is generally rectangular and has a width L31 and a height L32. The second section 358 is generally rectangular and has a width L31 and a height L33. The height L33 of the second section 358 is less than the height L32 of the first section 356. A recess 360, defined below the second section 358 and proximate the first section 356, extends into the body portion 332 a depth of L34 at the outer body surface 342 and has a height L35. The recess 360 may include an upper recess 360a and a lower recess 360b. The upper recess 360a is defined by a first recess wall 361, an upper recess surface 367, a lower recess surface 369, and the plane of the second section 358. The first recess wall 361 may have a generally curved profile and extends from the outer body surface 342 to the first section 356. The lower recess 360b is located below the upper recess 360a and extends into the body portion a distance L37 at the outer body surface 342. The lower recess 360b is defined by a second recess wall 371, the plane of the lower recess surface 369, the plane of the lower body surface 340, and the plane of the second section 358. The second recess wall 371 may have a generally curved profile and extends from the outer body surface 342 to the first section 356.

Figure 16:
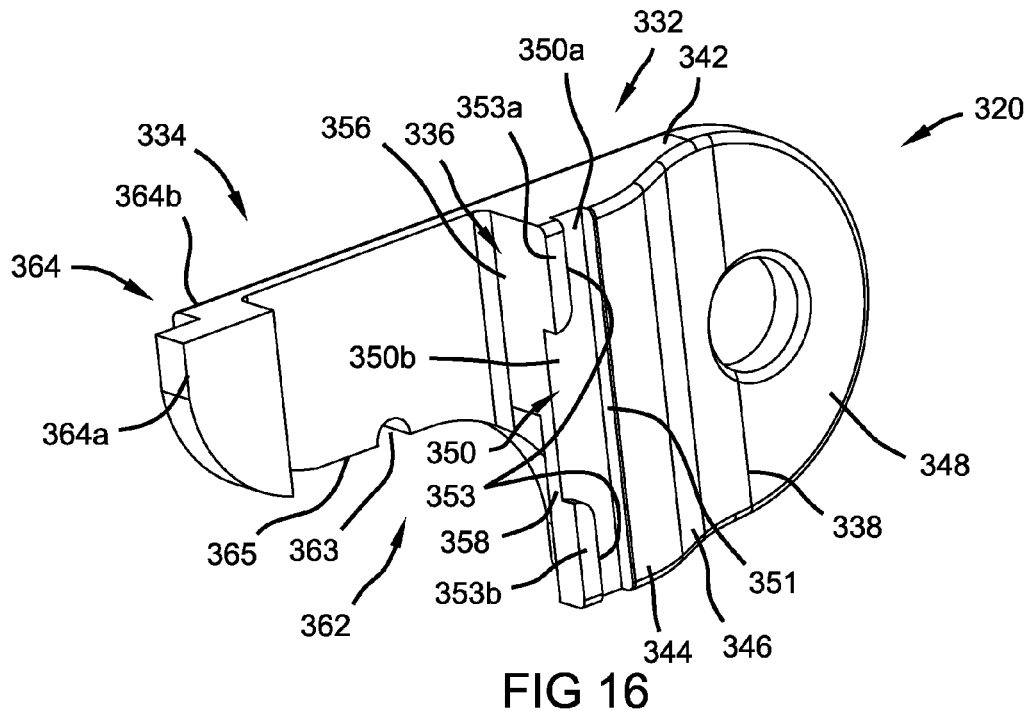
FIG. 16 is a front perspective view of one base part of the pectus bar stabilizer shown in FIG. 13 having an additional feature.
Figure 17:
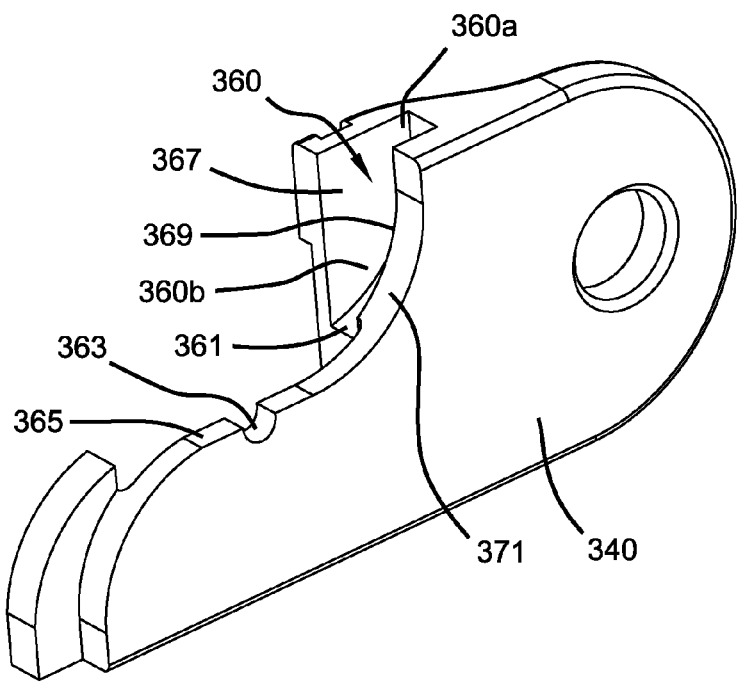
FIG. 17 is a rear perspective view of the base part of FIG. 16.

A leg 334 extends generally perpendicularly from the first section 356 of the inner body wall 336. The leg 334 may be divided into a first leg portion 362 and a second leg portion 364. The first leg portion 362, which is located proximate the body portion 332, may have a generally rectangular cross-section and a height less than the height L36 defined between the second section 358 and the lower body surface 340. The first leg portion 362 of the first and second base parts 320, 322 may also each include an arcuate recess 363 at an inner edge portion 365 as shown in FIGS. 16-17. The arcuate recess 363 may be optionally threaded (not shown). The second leg portion 364 may include a generally stepped arrangement having an upper portion 364a and a lower portion 364b. The upper portion 364a may have a shape similar to the shape of the upper recess 360a and the lower portion 364b may have a shape generally similar to the lower recess 360b, thereby allowing the second leg portion 364 to generally fit within the recess 360.

A series of apertures may be located in the first base part 320. A first aperture 352 may be located at a distal end 354 of the body portion 332, passing through the third section 348 of the top body surface 338 and the lower body surface 340. The first aperture 352 allows the first base part 320 to be coupled to a supporting structure, such as cartilage.

The retainer assembly 378 may include a retainer bar arrangement 382 and a stopping member assembly 384. The retainer bar arrangement 382 may include a series of legs 386 interconnected by a series of cross bars 387 extending between the legs 386 and generally perpendicular thereto, forming a channel 389 between the legs 386 and cross bars 387. The legs 386 may have end portions 391 extending beyond the cross bars 387. The legs 386 may generally have flattened, substantially rectangular cross-sections. The cross bars 387 may also generally have flattened, substantially rectangular cross-sections similar to those of the legs 386. The retainer assembly 378 may have a generally uniform thickness throughout its length. The legs 386 are located within the first recess 350a, extending generally parallel to the channel 312. The cross bars 387 may extend across the channel 312 and pass through the openings 350b in the inner wall 353.

The stopping member assembly 384 may include a tool 90, a neck portion 92 and a stopping member 94 similar to that described above. The pectus bar apertures 28, 30 may be threaded or the aperture 363 in the base parts 320, 322 may be threaded. If threading exists in either of these parts a screw may be used as the fastener and engage the threaded aperture. The stopping member 94 may include an additional portion extending beyond the threaded portion 110. This additional portion may be unthreaded to mate with recess 363 in FIGS. 16 and 17.

The pectus bar stabilizer assembly 310 may retain the pectus bar 12 through the first and second base parts 320, 322 and the retainer assembly 378. The two base parts 320, 322 may be placed proximate one another defining a channel 312 bound by the channel walls 336 and middle portion 362. In this configuration, the retainer recesses 350 of the first and second base parts 320, 322 are in respective alignment.

Once the first and second base parts 320, 322 have been arranged to define the channel 312, the retainer bar arrangement 382 may be placed in the retainer recess 350, thereby extending across the channel 312. The retainer bar arrangement 382 may then be welded in place. The retainer bar arrangement 382 secures the first and second base parts 320, 322 to one another in both a transverse direction and an axial direction relative to the retainer bar arrangement 382.

Once the first and second base parts 320, 322 are fixedly attached to one another, a first end portion 24 of the pectus bar 12 may be inserted into the channel 312. After the first end portion 24 is located within the channel 312, one of the apertures 28 in the first end portion may be aligned with the channel 389. After the desired aperture 28 is located below the channel 389, the stopping member 94 may be threaded, or otherwise fixedly secured, into the aperture 28. Once the stopping member 94 is securely in place, the tool 90 is separated from the stopping member 94 at the neck portion 92. The hexagonal head 104 may provide retention of the pectus bar 12. The body portion 106 of the stopping member 94 may be attached to the aperture 28 in the pectus bar 12. The hexagonal head 104 may extend above the pectus bar 12, providing for removal of the stopping member 94 from the pectus bar 12 if desired.

Other stopping members may be used for retention of the pectus bar 12 within the pectus bar stabilizer 314. One such example is a rivet, which may be applied to an aperture 28 in the pectus bar 12, leaving a head portion exposed above the pectus bar 12 to retain the pectus bar 12 within the pectus bar stabilizer 314 as described above.

The pectus bar 12 may be removed from the pectus bar stabilizer 314 without removing any of the stopping members 94. The retainer bar arrangement 382 may either partially or entirely removed. The pectus bar 12 may then translate axially free from the retainer bar arrangement 382. The stopping member 94 may also be removed, freeing the pectus bar 12 from the pectus bar stabilizer 314.

The pectus bar stabilizer 314 may generally be attached to an external structure, such as cartilage as previously discussed.

Figure 18:
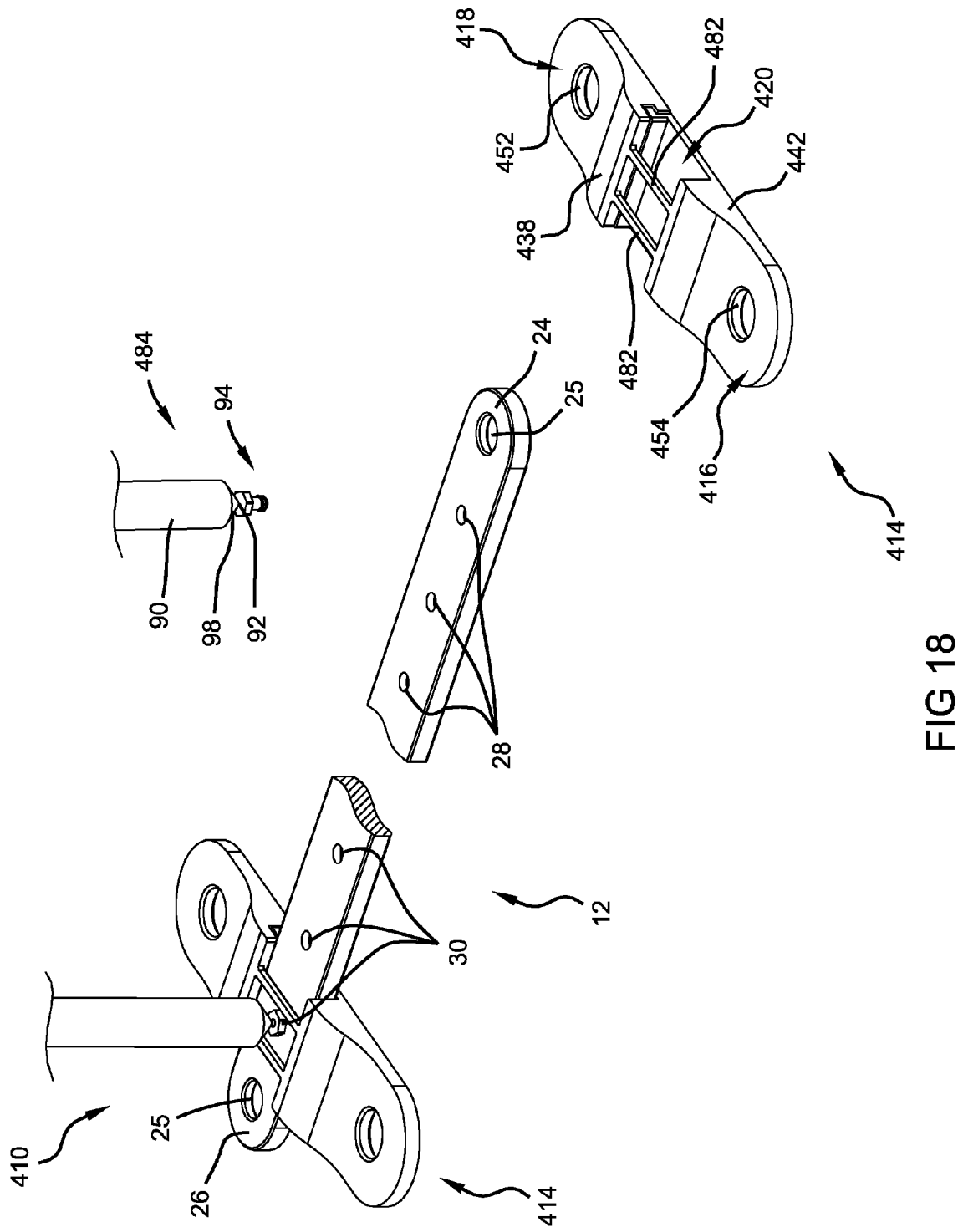
FIG. 18 is a perspective view of a pectus bar stabilizer assembly shown partially assembled and partially exploded.
Figure 19:
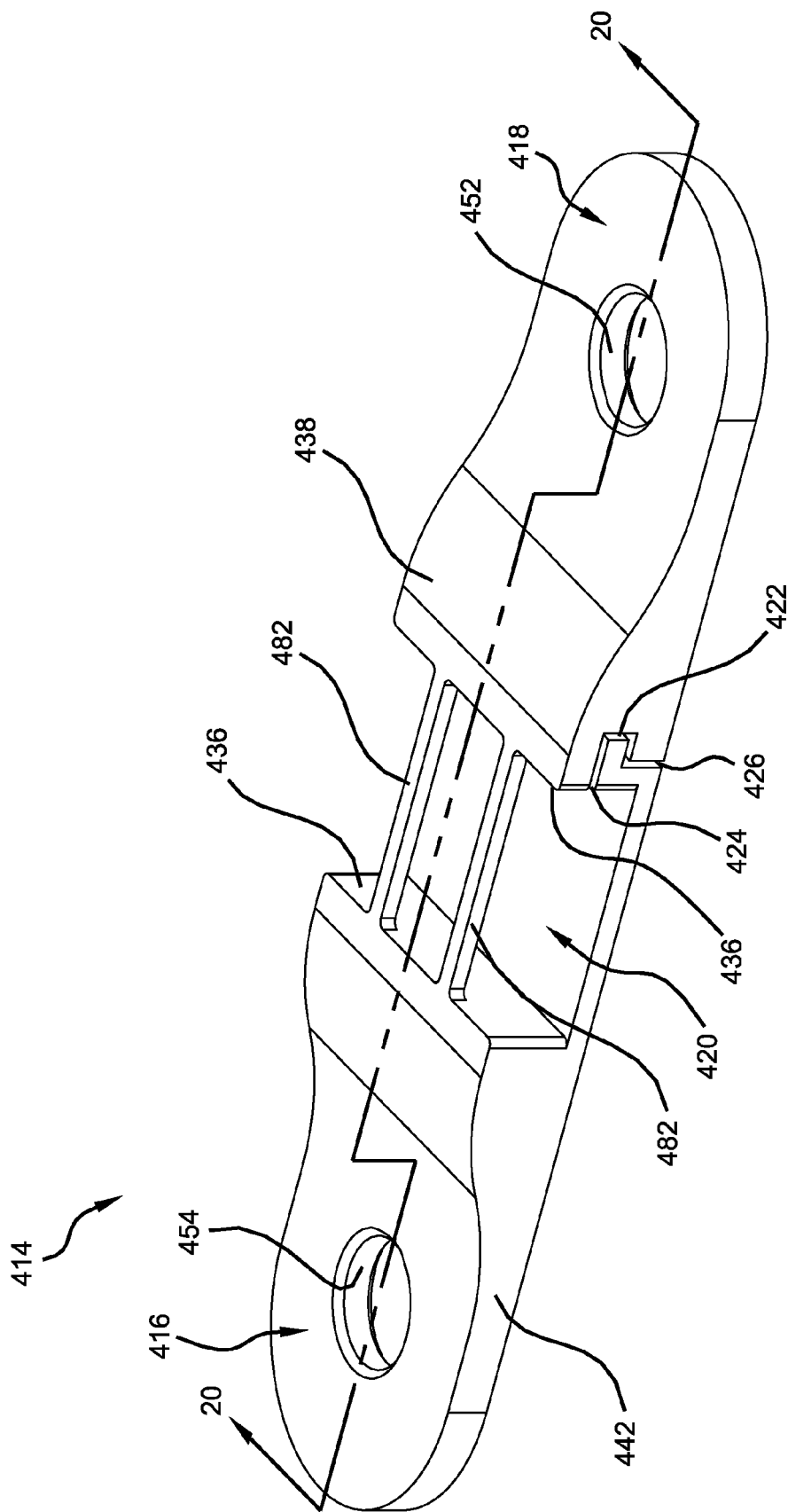
FIG. 19 is a perspective view of the pectus bar stabilizer of FIG. 18.
Figure 20:
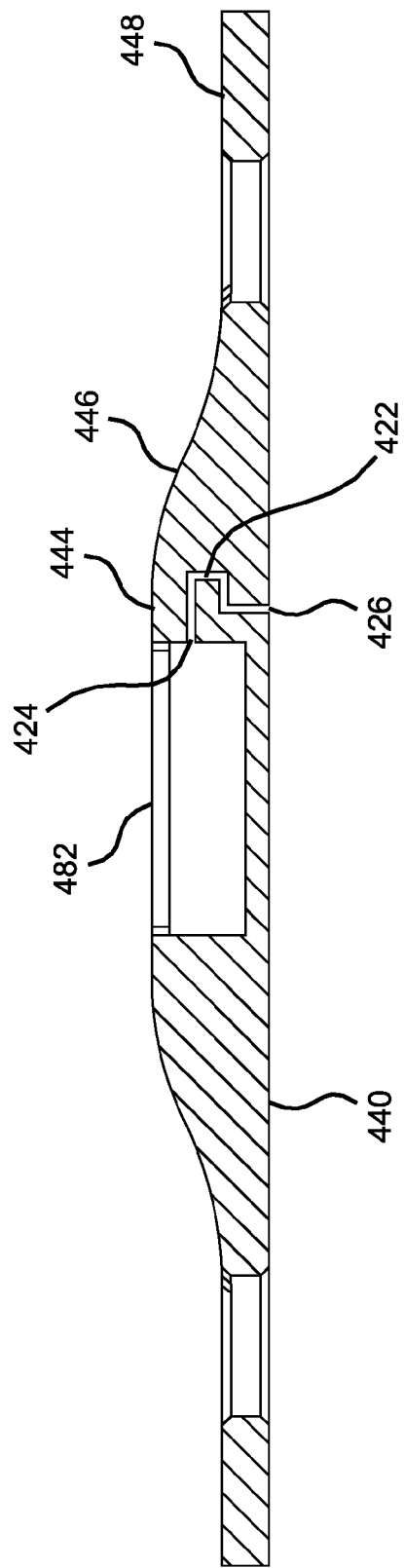
FIG. 20 is a sectional view of the pectus bar stabilizer of FIG. 19 taken at line 20-20.

An additional example of a pectus bar stabilizer assembly 410 is shown in FIGS. 18-20 and may generally include a pectus bar 12, a one-piece pectus bar stabilizer 414, and a stopping member assembly 484. The pectus bar stabilizer 414 retains the pectus bar 12 and may be fixedly attached to an external structure, such as cartilage.

The pectus bar stabilizer 414 may be machined as a single piece and include outer portions 416, 418 and a central recessed portion 420. The pectus bar stabilizer 414 may include inner body walls 436 defining central recessed portion 420. Pectus bar stabilizer 414 may further include top, lower, and outer body surfaces 438, 440, 442. Top body surface 438 may include three main sections 444, 446, 448. First section 444 may be generally planar. Second section 446 may be contoured and slope downward from first section 444 to third section 448. Third section 448 may be generally planar and extend from second section 446. Lower body surface 440 may be generally planar and parallel to first and third sections 444, 448 of top body surface 438. Outer body surface 442 may connect top body surface 438, lower body surface 440, and inner body wall 436. Central recessed portion 420 may additionally include a threaded or unthreaded aperture extending therethrough generally similar to the aperture created by unthreaded recess 63 in FIG. 9 or threaded recess 266 in FIG. 10.

A series of retaining bars 482 may be integrally formed with and extend between end portions 416, 418 and over central recessed portion 420. The retaining bars 482 may have flattened, generally rectangular cross-sections. The retaining bars 482 may have a generally uniform thickness throughout their length.

A series of apertures 452, 454 may be located in outer portions 416, 418, passing through third section 448 of top body surface 438 and lower body surface 440. Apertures 452, 454 allow pectus bar stabilizer 414 to be coupled to a supporting structure, such as cartilage.

A channel 422 may be located in pectus bar stabilizer 414. Channel 422 may have a starting point 424 located below and generally between ends of retaining bars 482. As shown in FIG. 19, starting point 424 may extend through inner body wall 436. An end point 426 of channel 422 may extend through lower body surface 440. Channel 422 may take the form of a variety of paths allowing separation of outer portions 416, 418 once retaining bars 482 are severed, as discussed below. Channel 422 may be formed in a variety of ways, such as wire electrical discharge machining (EDM).

Stopping member assembly 484 may include a tool 90, a neck portion 92 and a stopping member 94 similar to that described above. Stopping member 94 may include an additional portion extending beyond threaded portion 110, similar to that shown in FIGS. 7 and 10. This additional portion may be threaded for mating with a threaded aperture or unthreaded to pass through an unthreaded aperture in central recessed portion 420.

A first end portion 24 of pectus bar 12 may be inserted into recessed portion 420 below retaining bars 482. After first end portion 24 is located within central recessed portion 420, one of apertures 28 may be located between retaining bars 482, stopping member 94 may then be threaded, or otherwise fixedly secured, into aperture 28. Once stopping member 94 is securely in place, tool 90 may be separated from stopping member 94 at neck portion 92. Hexagonal head 104 may provide retention of pectus bar 12. Body portion 106 of stopping member 94 may be attached to aperture 28 in pectus bar 12. Hexagonal head 104 may extend above pectus bar 12, providing for removal of stopping member 94 from pectus bar 12 if desired.

Other stopping members may be used for retention of pectus bar 12 within pectus bar stabilizer 414. One such example is a rivet, which may be applied to an aperture 28 in pectus bar 12, leaving a head portion exposed above pectus bar 12 to retain pectus bar 12 within the pectus bar stabilizer 414 as described above.

Pectus bar 12 may be removed from pectus bar stabilizer 414 without the removal of stopping members 94. Retaining bars 482 may be severed resulting in outer portions 416, 418 being separated from one another due to channel 422. Pectus bar 12 may then be removed from pectus bar stabilizer 414 while still having stopping member 94 therein.

The description is merely exemplary in nature and, thus, variations are not to be regarded as a departure from the spirit and scope of the present teachings.

What is claimed is:

1. A minimally invasive surgical method comprising:
accessing an assembly attached to tissue within a human body, the assembly including a pectus bar, a stabilizer member and a stopping member, the stabilizer member having first and second base parts defining a channel receiving the pectus bar and first and second retaining bars extending between the first and second base parts and traversing the channel, the stopping member attached to the pectus bar between the first and second retaining bars and restricting movement of the pectus bar within the channel;
severing one of the first and second retaining bars; and
removing the pectus bar from the channel of the stabilizer member with the stopping member attached to the pectus bar.

2. The minimally invasive surgical method of claim 1, wherein the one of the first and second retaining bars is severed with the stabilizer member attached to tissue of the human body.

3. The minimally invasive surgical method of claim 1, wherein the stopping member includes a body portion and a head portion, and wherein the pectus bar is removed from the channel without disengaging the body portion of the stopping member from the stabilizer member.

4. The minimally invasive surgical method of claim 3, wherein the body portion of the stopping member does not directly engage the stabilizer member prior to removing the pectus bar from the stabilizer member.

5. The minimally invasive surgical method of claim 1, further comprising severing the other of the first and second retaining bars.

6. The minimally invasive surgical method of claim 1, wherein said stopping member is a rivet.

7. The minimally invasive surgical method of claim 1, wherein said stopping member is a screw.

8. The minimally invasive surgical method of claim 1, wherein the first and second retaining bars are substantially parallel to each other.

9. The minimally invasive surgical method of claim 1, wherein the stopping member is received in a selected one of a plurality of apertures formed in the pectus bar.

10. A minimally invasive surgical method comprising:
   accessing an assembly attached to tissue within a human body, the assembly including a pectus bar, a stabilizer member and a stopping member, the stabilizer member having first and second base parts defining a channel receiving the pectus bar and first and second retaining bars extending between the first and second base parts and traversing the channel, the stopping member attached to the pectus bar between the first and second retaining bars and restricting movement of the pectus bar within the channel;
   disengaging the first and second base parts from each other; and
   removing the pectus bar from the stabilizer member with the stopping member attached to the pectus bar.

11. The minimally invasive surgical method of claim 10, wherein disengaging the first and second base parts from each other includes severing at least one of the first and second retaining bars.

12. The minimally invasive surgical method of claim 11, wherein the one of the first and second retaining bars is severed with the stabilizer member attached to tissue of the human body.

13. The minimally invasive surgical method of claim 10, wherein the stopping member includes a body portion and a head portion, and wherein the pectus bar is removed from the channel without disengaging the body portion of the stopping member from the stabilizer member.

14. The minimally invasive surgical method of claim 13, wherein the body portion of the stopping member does not directly engage the stabilizer member prior to removing the pectus bar from the stabilizer member.

15. The minimally invasive surgical method of claim 10, further comprising severing the other of the first and second retaining bars.

16. The minimally invasive surgical method of claim 10, wherein said stopping member is a rivet.

17. The minimally invasive surgical method of claim 10, wherein said stopping member is a screw.

18. The minimally invasive surgical method of claim 10, wherein disengaging the first and second base parts from each other includes removing the first and second retaining bars from the stabilizer member.

19. The minimally invasive surgical method of claim 10, wherein the first and second retaining bars are substantially parallel to each other.

20. The minimally invasive surgical method of claim 10, wherein the stopping member is received in a selected one of a plurality of apertures formed in the pectus bar.

* * * * *